United States Patent [19]

Trafford

[11] Patent Number: 4,728,434
[45] Date of Patent: Mar. 1, 1988

[54] LIQUID CHROMATOGRAPHY

[75] Inventor: Paul F. Trafford, Northampton, United Kingdom

[73] Assignee: Magnetopulse Limited, Northants, United Kingdom

[21] Appl. No.: 10,854

[22] Filed: Feb. 4, 1987

[51] Int. Cl.⁴ .......................................... B01D 15/08
[52] U.S. Cl. .................................... 210/656; 210/101; 210/198.2; 222/57; 222/134; 366/160
[58] Field of Search ...................... 210/656, 659, 198.2, 210/101; 222/52, 55, 57, 134; 366/160

[56] References Cited

U.S. PATENT DOCUMENTS

| | | | |
|---|---|---|---|
| 3,398,689 | 8/1968 | Allington | 210/101 |
| 4,045,343 | 8/1977 | Achener | 210/101 |
| 4,128,476 | 12/1978 | Rock | 210/101 |
| 4,310,420 | 1/1982 | Konishi | 210/101 |
| 4,311,586 | 1/1982 | Baldwin | 210/101 |
| 4,347,131 | 8/1982 | Brownlee | 210/101 |
| 4,422,942 | 12/1983 | Allington | 210/101 |
| 4,478,713 | 10/1984 | Girot | 210/101 |
| 4,595,495 | 6/1986 | Yotam | 210/101 |
| 4,595,496 | 6/1986 | Carson | 210/101 |

*Primary Examiner*—Ernest G. Therkorn
*Attorney, Agent, or Firm*—Sherman and Shalloway

[57] ABSTRACT

In a process of liquid mixing, more especially for use in mixing the solvents of an eluent for liquid chromatography, the liquids are supplied from separate reservoirs (1–4) to a common conduit (13) via fluid flow control valves (5–8). Predetermined pressure drops are maintained across each valve by arranging appropriate pressures in the reservoirs (1–4) and the conduit (13). The rate of flow of each liquid is determined by setting each valve (5–8) to present a predetermined flow resistance calculated from the formula $$L \alpha \sqrt{\frac{\Delta H/S}{I}}$$

where L=the flow resistance of the valve $\Delta H$=the pressure drop across the valve S=the specific gravity of the liquid and I=the desired rate of flow of the liquid. The calculation and automatic actuation of the valves is effected by an electronic control (14) incorporating a microprocessor which may be programmed to vary the liquid mixture with time to provide a desired elution gradient.

4 Claims, 3 Drawing Figures

LIQUID CHROMATOGRAPHY

This invention concerns improvements in liquid chromatography, more especially so-called high performance liquid chromatography.

The process of high performance liquid chromatography is well-known to those skilled in the art, and will therefore not be described in detail. One particularly effective technique used in this process is that of gradient elution wherein the strength of the mobile phase is increased during a chromatographic analysis. The formation of an appropriate gradient is achieved in practice by varying the proportions of a mixture of solvents supplied to the chromatographic column, so that the relative proportions of the solvents in the mixture reaching the column varies with respect to time, either stepwise or in a continuous manner.

The known processes for mixing solvents to achieve the required gradient have a number of disadvantages.

In one arrangement, solvents are supplied to a mixing chamber on the upstream side of a pump serving the chromatographic column by way of a proportioning valve which periodically opens and closes conduits from each solvent reservoir to the mixing chamber. The period of time for which each responsive conduit is open is controlled electronically, thus controlling the average composition of the eluent reaching the mixing chamber, and thus the composition of the eluent reaching the pumping system. Such an arrangement has the disadvantage that a relatively large mixing chamber is necessary in order to average the mixture of eluent from the discrete doses of solvent supplied via the mixing valve, which results in the wastage of relatively large amounts of solvent, and the corresponding increase in analysis time. Moreover, the arrangement is complex to operate when more than two solvents are required and mixing problems can occur if the operation of the system is not synchronised to match the characteristics of the solvent pump.

In another system, the respective solvents are each supplied from a reservoir via a separate pump which is controllable to vary the volume of liquid pumped with respect to time. The outlets of the pumps are connected to a common conduit via a T junction, so that mixing of the solvents occurs on the downstream side of the pump, the proportions of the mixture being determined by the relative flow rates of the two pumps. The flow rates of the pumps are controlled electronically in such a manner that the total flow of liquid is always constant, although the proportion of the respective solvents can be varied. Such an arrangement has the disadvantage that the pumps are required to be of very high accuracy in order to provide the require accuracy of mixing, and are correspondingly relatively expensive. The use of such a system is thus in practice limited to a two solvent mixture, since the cost of multiple pumps for a greater number of solvents would be prohibitive.

It is an object of the present invention to provide a novel system for the accurate mixing of solvents in the process of gradient elution, which avoids, or at least reduces, at least some of the disadvantages outlined above.

In accordance with the present invention there is provided a method of liquid chromatography utilising a mixture of liquid solvents of which the mixed proportions are to be varied during the elution process, wherein the respective solvents are supplied to the upstream side of a single pump serving the chromatographic column, in each case from a separate liquid reservoir, there is provided between each reservoir and a corresponding supply conduit communicating with the suction side of the pump a control valve providing a variable resistance to liquid flow, a predetermined liquid pressure drop is maintained across each control valve for the corresponding solvent, and the flow resistances presented by the respective control valves are charged with respect to time, by corresponding adjustment of said valves, in order to produce a desired variation in the rate of flow of each solvent.

The process of the present invention is based upon the appreciation that, for liquid with viscosities which are less than or close to that of water, which is the case for all eluent liquids which are in practice used in high performance liquid chromatography, the rate of flow of the liquid through an orifice having a given resistance is substantially only dependent upon the pressure difference across the restriction and the density of the solvent. This relationship is set out in the following formula $$I \propto \frac{\sqrt{\Delta H / S}}{L}$$

where
I = Flow Rate
$\Delta H$ = Differential Pressure
S = Specific Gravity
L = Resistance to Fluid Flow Thus, with appropriate control of the relationships between the fluid pressures under which the respective solvents are supplied to the corresponding control valves, and/or the relationship between the corresponding adjustments of the respective control valves, any desired elution gradient involving any desired number of eluents can be achieved simply by corresponding adjustment of the respective control valves.

In practice the control valves may be simple needle valves coupled by an appropriate mechanical transmission to electronically controlled stepping motors, the stepping motors being controlled from an electronic programming system in such a manner as to achieve the desired variation in the solvent mixture.

The invention is illustrated by way of example in the accompanying drawings, in which:

DESCRIPTION OF THE PREFERRED EMBODIMENTS

Figure 1:
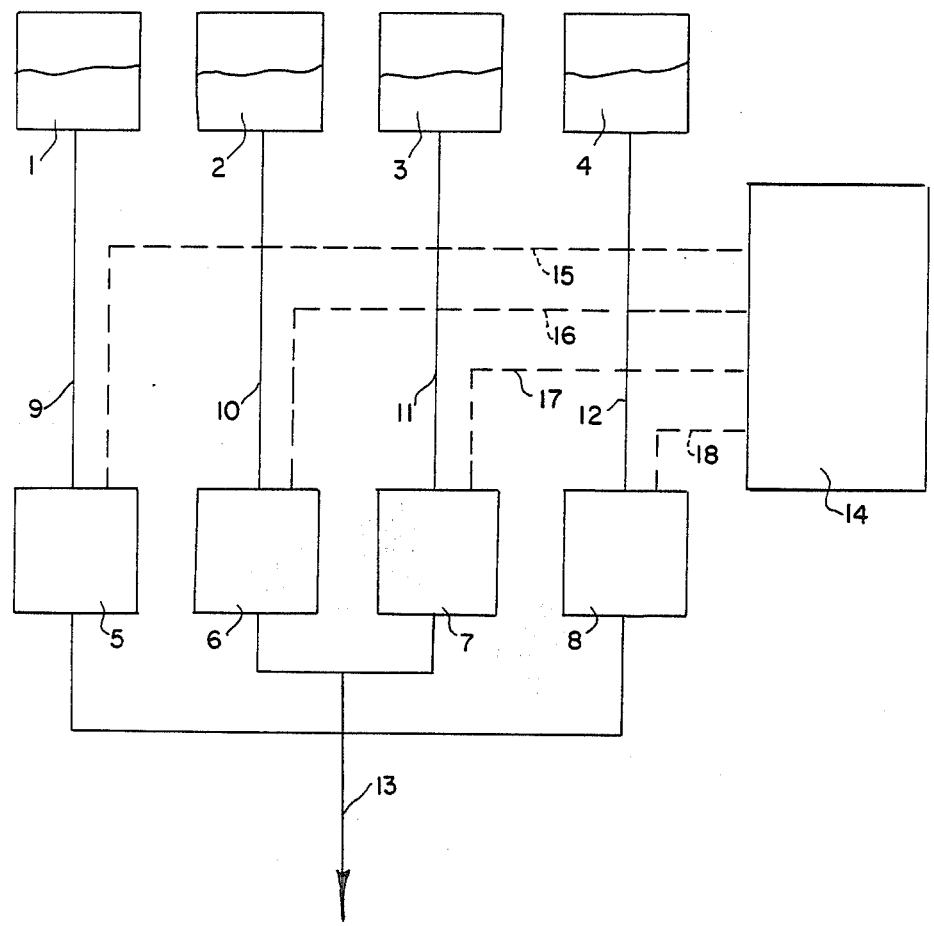
FIG. 1 is a diagrammatic view of one liquid mixing arrangement in accordance with the invention.

Referring to FIG. 1, a plurality, for example, four, solvents to form an eluent mixture are provided in corresponding liquid reservoirs 1 to 4, within which the prevailing fluid pressure is maintained at some pressure above atmospheric. Each liquid reservoir is arranged to supply a corresponding control valve, for example, a needle valve, indicated diagrammatically at 5 to 8, via a corresponding conduit 9 to 12. The downstream side of the control valves 5 to 8 are coupled via a 5-way T junction to a conduit 13 coupled to the inlet of a liquid pump, not shown, which is arranged to serve a chromatographic column in a manner well-known in the art. Each of the control valves 5 to 8 is arranged to be adjusted in response to signals from an electronic control system 14. The broken lines 15 to 18 indicate diagrammatically a servo control connection between the control system 14 and each of the valves 5 to 8.

As already explained above, the rate of flow of each of the solvents from the reservoirs 1 to 4 through the corresponding valves 5 to 8 will depend in each case upon the resistance provided by the needle valve, which is in turn a function of the degree of adjustment thereof effected by the control system 14, the specific gravity of the respective solvent, and the pressure drop across the respective valve, that is to say the difference in the fluid pressures prevailing in the respective one of the conduits 9 to 12, on the one hand, and the conduit 13 on the other hand. If this pressure drop is arranged to be same in each case, for example by arranging the liquid reservoirs 1 to 4, the valves 5 to 8 and the liquid pump all on the same level so that there is effectively no head of liquid on the upstream side of the pump, then the rate of flow of liquid in each case will be a function solely of the specific gravity of the respective liquid and the flow resistance presented by the respective control valve. Therefore, the liquids can be mixed in the desired proportions simply by correspondingly controlling the adjustment of the respective needle valve 5 to 8 after adjusting the degree of opening in accordance with a correction factor determined by the density of the respective liquid.

Figure 2:
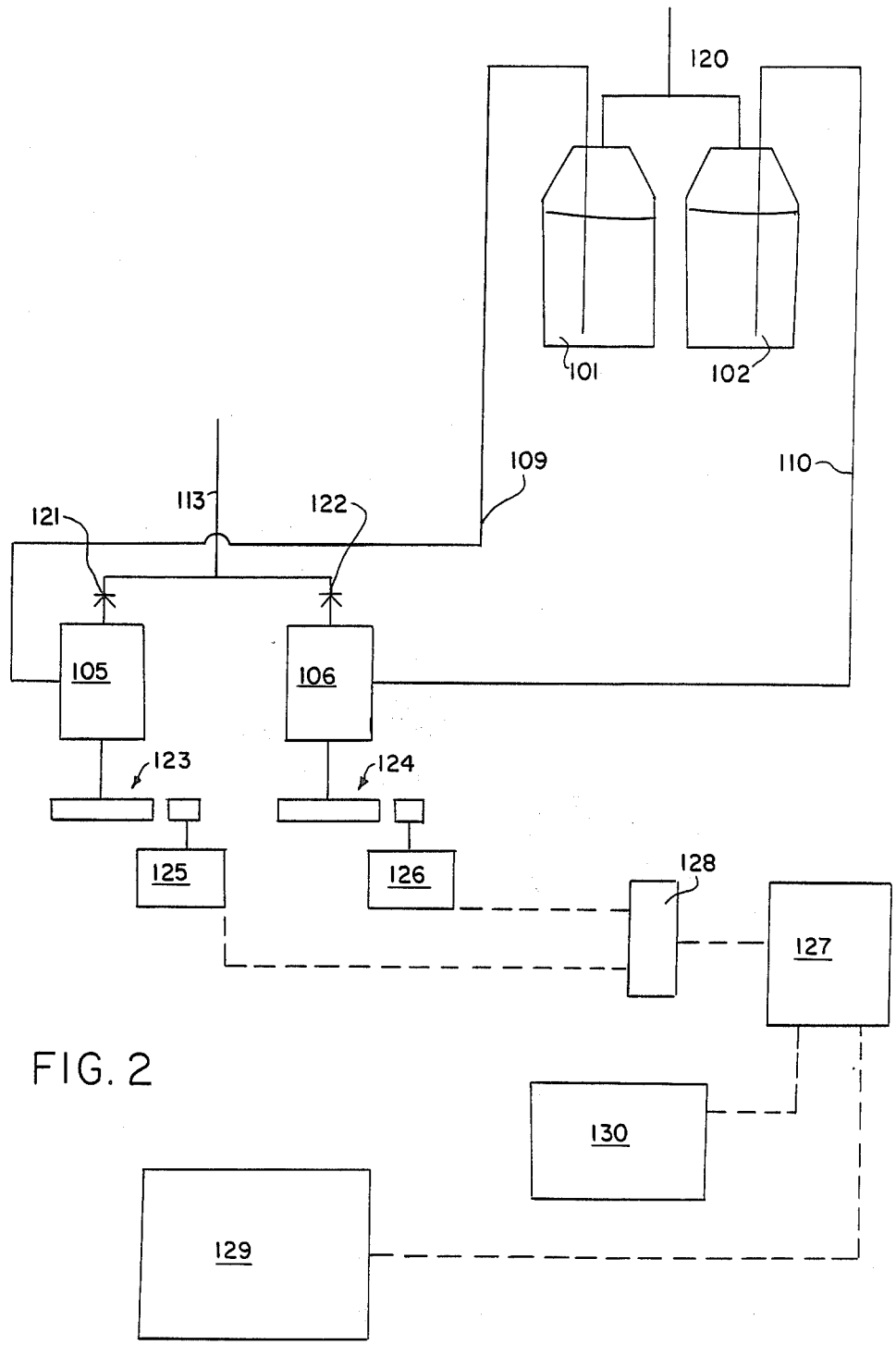
FIG. 2 is a similar view of another arrangement in accordance with the invention.

Referring now to FIG. 2, there will be described one specific example of the process in accordance with the invention. Two solvent reservoirs indicated diagrammatically at 101 and 102 were arranged on the same level as a liquid pump (not shown) feeding a chromatographic column, so that there was no head of liquid on the upstream side of the pump. The pump utilised in this example was a known chromatographic solvent pump supplied by H. P. L. C. Technology Limited, Type No. R R 065. The solvent reservoirs 101 and 102 comprise closed containers of which the free space unfilled by liquid was coupled to a source of gas pressure at 10 p.s.i. (0.67 bar) via a conduit 120. Liquid supply conduits 109 and 110 coupled the solvent reservoirs to the inlet side of corresponding needle valves 105 and 106 of which the outlets were coupled via a tee piece to a conduit 113 coupled to the upstream side of the liquid pump. Check valves 121 and 122 were provided between the needle valve and the tee piece to avoid syphoning of the solvent back into reservoirs 101 and 102 with the liquid pump in the idle condition. The needle valves 105 and 106 were coupled by a gearing indicated diagrammatically at 123 and 124 to stepping motors 125 and 126 of which the position could be controlled by way of a microprocessor 127 via an interface 128. The microprocessor was associated with a keyboard 129 and video display unit 130.

In the examples to be described, the solvent contained in the reservoirs 101 and 102 was methyl alcohol of which one sample was colourless, and the other was provided with an ultraviolet light absorbing dye. The microprocessor 127 was caused to adjust the stepper motors 125 and 126 with respect to time according to a software programme which caused the settings of the needle valves 105 and 106 to be adjusted relatively to one another in order to change the composition of the solvent reaching the conduits 113 from one percent to 99% of the dye containing solvent in one percent steps. The absorbancy of the resulting eluent at 300 nanometers wavelength was monitored by an ultraviolet detector type LC3 supplied by Pye Unicam Limited, the output signal from the detector being utilised to control a chart recorder in known manner.

Figure 3:
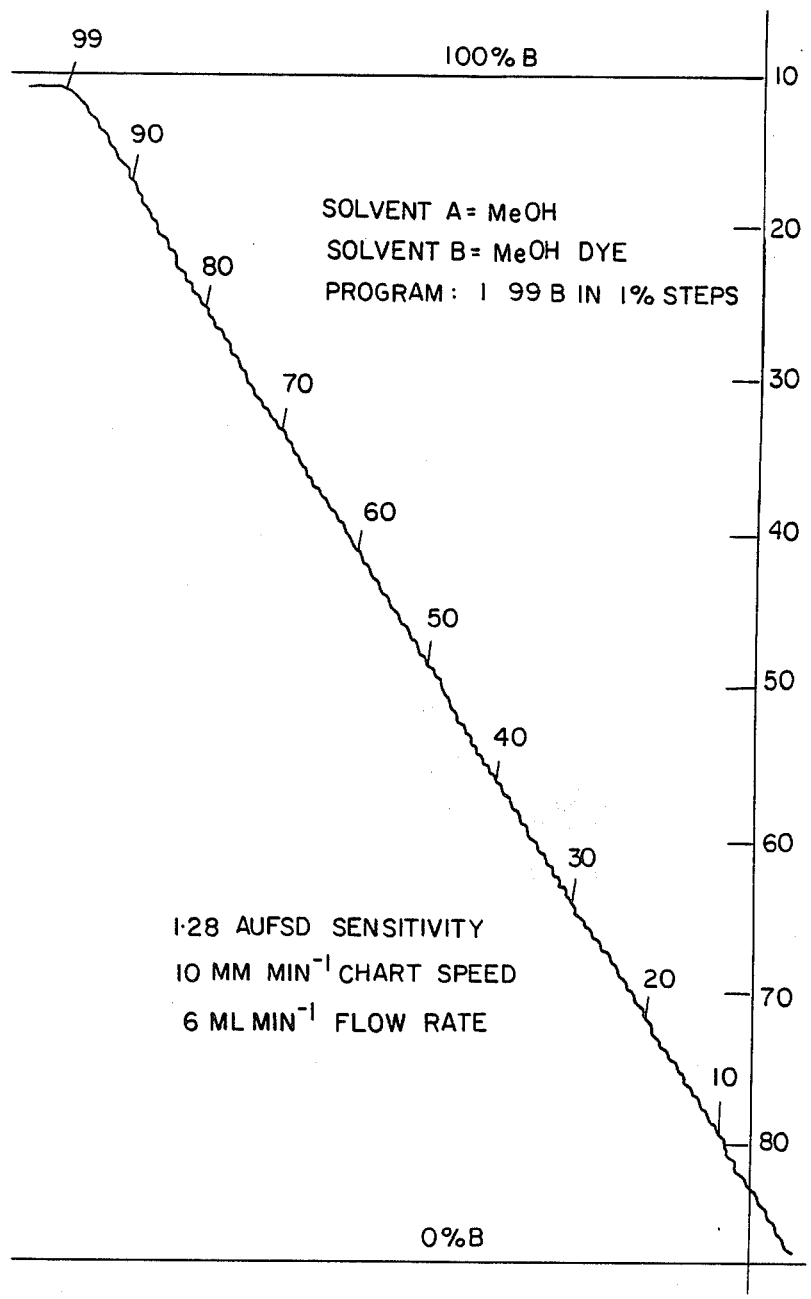
FIG. 3 is an illustration of a chromatograph produced in one example of a process according to the invention.

Since the solvent contained in both reservoirs 101 and 102 was the same, no adjustment of the control programme to take account of relative specific gravity of the solvent was necessary, and the needle valves 105 and 106 were simply adjusted so that the respective flow resistances varied inversely with respect to one another to give a constant liquid flow rate to the pump of 6 ml per minute. The resulting chromatograph is indicated in FIG. 3. Thus it will be seen that simply by servo-controlled actuation of the needle valves 105 and 106, an accurate adjustment of the relative proportions of the solvent in the mixture was obtained, without the requirement for the use of a large volume mixing chamber, and without the need for expensive variable volume pumps to control the flow of each liquid.

It will be appreciated that various modifications to the invention as described may be made without departing from the scope thereof. For example, although in the example illustrated the pressure drop across each needle valve was the same for each liquid, it will be appreciated that these pressures may differ provided that a corresponding allowance is made for this factor when adjusting the control valve. In a particularly advantageous arrangement, the need to correct the settings of the control valves to compensate for the use of liquid of different density may be avoided when the liquid supply reservoirs are so arranged that a positive head of liquid is present on the upstream side of each control valve, the head of liquid being maintained the same in each case, so that the pressure drop across each control valve is directly proportional to the specific gravity of the corresponding liquid. An appropriate mechanism is thus arranged to compensate for the different volumes of solvent supplied from the respective reservoirs. For example, a float valve may supply solvent to each reservoir at the same rate as it is withdrawn therefrom.

I claim:

1. A method of mixing solvents providing an eluent in a process of liquid chromatography in order to provide a predetermined elution gradient having a desired rate of flow and containing a plurality of liquids in desired proportions, wherein the respective liquids are each supplied to a common conduit via an adjustable flow control valve presenting a resistance to fluid flow that varies in a known relationship to the setting of the valve, a predetermined pressure drop ($\Delta H$) is maintained for each liquid across the corresponding control valve, and each valve is adjusted to a setting corresponding to a predetermined known flow resistance (L) in order to produce a corresponding rate of flow (I) of the liquid through the control valve such that the relationship between the individual rates of flow of the respective liquids corresponds to the desired proportions of the liquids in the final mixture and the total of the individual rates of flow corresponds to the desired rate of flow of the liquid mixture, the setting position of each valve being determined by calculation according to the formula $$L \alpha \sqrt{\frac{\Delta H/S}{I}}$$

where S is the specific gravity of the liquid flowing through the valve.

2. A method as claimed in claim 1, wherein the fluid flow control valves are actuated by stepper motors under the control of a microprocessor programmed to calculate the correspondingly required positions of the control valves.

3. A method as claimed in claim 2, wherein the fluid flow control valves comprise needle valves.

4. A method as claimed in any one of claims 1-3, wherein the pressure drop ($\Delta H$) is maintained the same for all said liquids.

* * * * *